United States Patent [19]

Klesius et al.

[11] 4,180,627

[45] Dec. 25, 1979

[54] PROCESS FOR IN VIVO TRANSFER OF CELL-MEDIATED IMMUNITY IN MAMMALS WITH ALCOHOLIC PRECIPITATES OF BOVINE TRANSFER FACTOR

[75] Inventors: Phillip H. Klesius, Auburn, Ala.; Herman H. Fudenberg, Charleston, S.C.

[73] Assignee: The United States of America as represented by the Secretary of Agriculture, Washington, D.C.

[21] Appl. No.: 934,289

[22] Filed: Aug. 17, 1978

[51] Int. Cl.$^2$ .................. C07G 7/00; A61K 39/00
[52] U.S. Cl. .................................. 435/262; 435/272; 424/88; 424/95
[58] Field of Search ................ 195/1, 29; 424/88, 105

[56] References Cited

PUBLICATIONS

Lawrence, Journal of Clinical Investigation, vol. 34, pp. 219–230 (1955).
Lawrence, in "Transfer Factor: Basic Properties and Clinical Applications", pp. 741–753 (1976), Ascher, et al., editors.
Klesius, et al., in Transplantation Proceedings, vol. VII (3), pp. 449–452, (1975).
Klesius, et al., in Clinical Immunology and Immunopathology, vol. 7, pp. 240–252 (1977).
Klesius, et al., in "Transfer Factor: Basic Properties and Clinical Applications", pp. 311–322 (1976).

*Primary Examiner*—Lionel M. Shapiro
*Attorney, Agent, or Firm*—M. Howard Silverstein; David G. McConnell

[57] ABSTRACT

Precipitates soluble in aqueous solution and suitable for stimulation and/or transfer of cell-mediated immunity in mammals and other animals is disclosed together with a solvent extraction process for obtaining this desirable product from crude bovine transfer factor. Lymphocytes from lymph nodes and blood of donor cattle are employed in formulating a Bovine Transfer factor by incubation release procedure. The fractionation of Bovine Transfer factor yields three precipitate fractions by the use of organic solvents. A relatively high incidence of transfer with the precipitates yields excellent immunity to certain diseases in animals.

4 Claims, No Drawings

PROCESS FOR IN VIVO TRANSFER OF CELL-MEDIATED IMMUNITY IN MAMMALS WITH ALCOHOLIC PRECIPITATES OF BOVINE TRANSFER FACTOR

BACKGROUND OF THE INVENTION (1) Field of the Invention

This invention relates to aqueous soluble precipitates that can stimulate or transfer cell-mediated immunity and to the production thereof from unfractionated bovine transfer factor.

(2) Description of the Prior Art

The prior art teaches that it is not possible to transfer cell-mediated immunity (delayed skin hypersensitivity reaction) with serum. However, viable lymphocytes taken from a reactive person and transferred to a non reactive person will temporarily make the recipient reactive, that is, tuberculin-positive. In man—but not in animals—it is also possible to transfer reactivity of "delayed" reactivity by means of nonviable extracts from lymphocytes. This means, this material, has been referred to as "transfer factor". See Lawrence, H. S. J. Clin. Invest, 219, 34 (1955) and Lawrence H. S. in "Transfer Factor: Basic Properties and Clinical Applications", p. 741 (Ascher, Gottlieb, and Kirkpatrick editors), Academic Press, New York, 1976.

In the prior art Phillip H. Klesius, et al., in Transplanation Proc. VII(3), 449–452, 1975, disclosed the first isolation of transfer factor from cattle lymphocytes. The bovine transfer factor in crude form, stimulated or transferred cell-mediated immunity across species barriers.

The literature discloses that unfractionated bovine transfer factor stimulates or transfers cell-mediated immunity against certain diseases in animals. The efficiency of the unfractionated bovine transfer factor was limited. [See "Bovine Transfer Factor, Isolation and Characteristics" by Phillip H. Kleusius, et al., in "Transfer factor: Basic Properties and Clinical Applications," p. 311 (Ascher, Gottlieb, and Kirkpatrick Editors) Adacemic Press, New York, 1976.]

The teachings of the prior art characterized bovine transfer factor as having properties and characteristics similar to that of human transfer factor. The disadvantage of human material obtained from a single donor in comparison to larger yields obtained from single donor cow. See Klesius, P. H., et al., Clinical Immunology and Immunopathology, 7, p. 240–252, 1977.

There is no known commercial method for the solvent extraction of bovine transfer factor to produce active precipitates with all the characteristics of the present invention. The prior art teaches that liquid chromatography and electrophoresis have yielded small amounts of transfer factor which makes these methods impractical to use as a means of commercial extraction.

The Review of Medical Microbiology, 11th edition, compiled by Drs. Ernest Jawetz, Joseph L. Melnick, and Edward A. Adelberg, provides a brief review of the various facets of pertinent data which would enlighten the reader of the present specification.

SUMMARY OF THE INVENTION

Lymphocytes obtained from specific area of the lymphatic system of donor cattle are ground, then separated to discard the unwanted solids and utilize the liquid portion in the preparation of a culture. The lymphocytes contained in this liquid portion are incubated in Hank's balanced salt solution. Cell viability is verified by trypan blue exclusion, and the viability would decrease by 60% to 70% during the incubation period. The incubated material is separated by centrifugation. The supernatant culture fluid is dialyzed against deionized water; the dialysate is lyophilized; and the resulting dry material is designated "unfractionated Transfer Factor, (TF)".

The improvement of the process begins when the TF is dissolved in water, the pH adjusted to about 6.0 to 6.5, and fractionated with alcohol. All steps of fractionation are carried out throughout at about 4° C. Alcohol is added dropwise to form an alcohol-water interface, which is fibrous. The mixture is stirred and the precipitate removed. The supernatant fluid is separated and the pelleted precipitate drained and dissolved in water, and lypholized to obtain Fraction I.

Alcohol is added to the supernatant, dropwise, as before, to obtain a second interface, which is then stirred and separated as before, thus yielding a precipitated Fraction II. The combined two precipitates, I and II fractions, are useful in intraperitoneal and intramuscular subcutaneous injections and oral ingestion to stimulate or transfer cell-mediated immunity in mammals.

The fractions I or II alone were active in stimulating cellmediated immunity. Although, it appears that the fraction II precipitate contains most of the material responsible for transfer factor activity, fraction I is also active in stimulating cellmediated immunity.

The primary object of the present invention is to provide a safe, nontoxic, microbial-free fraction of transfer factor that has a high rate conversion or efficiency (80% or better) for causing cell-mediated reactivity in mammals. The alcohol fractionation procedure provides a product that has not been denatured and is soluble in aqueous or physiological solution for treatment of mammals by multi-routes.

Another object is to provide a large amount of fractionated transfer factor that can be rapidly prepared from cattle that have been specifically sensitized for cell-mediated immunity against certain diseases. Still another object is to provide a solvent extracted transfer factor to be produced continuously on a commercial scale from the donor cattle and use in mammals to stimulate their cell-mediated immunity against the disease to which the cattle were sensitized.

DESCRIPTION OF THE PREFERRED EMBODIMENTS

In the practice of the present invention, prior art fractionation techniques, such as liquid chromatography and electrophoresis yielded lower amounts of transfer factor that may be contaminated with organic solvents toxic to mammals.

The bovine transfer factor is prepared from cattle sensitized for specific cell-mediated reactivity against the immunizing antigen(s). Blood or node lymphocytes are separated from unwanted tissue or debris.

The lymphocytes are cultured in Hank's balanced salt solution for a period of at least 4 hours at 37° C. By means of this incubation-release method the transfer factor material is separated from the lymphocytes (90% or better).

The unwanted large molecular ($<15,000$) weight material of the resulting cell-free culture supernatant is removed by dialysis against deionized water or by ultrafiltration. Following this treatment the unfractionated transfer factor is extracted by the solvent step, using food-grade solvent such as ethenol is suitable. A typical solvent to transfer factor ratio for the first precipitate, Fraction I, is about 2 to 1 volumes. Extraction temperatures usually are about 4° C. For the second precipitate, Fraction II, the ratio is usually 4 to 1 volumes.

The final product is white or colorless and nontoxic for mammals. The product is soluble in aqueous or physiological solutions and is very active in stimulating or transferring cell-mediated immunity specifically or nonspecifically to mammal recipients.

The present invention generally is applicable to all mammalian species of animal including man.

The following example is provided to illustrate the process and product of this invention, and should not be construed as limiting the invention in any manner whatever.

EXAMPLE

Animals:

Calves 4 to 6 months of age were housed in individual pens or on concrete enclosures and maintained under management practices devised to prevent parasitic infection, especially coccidiosis.

Bovine donors for dialyzable transfer factor ($TF_d$)

Selection of donor cattle was based on positive skin reactions and in vitro lymphocyte stimulation responses to the test antigens. $TF_d$ donors for *E. bovis* antigen and Purified Protein Derivative (PPD) were first infected with 100,000 *E. bovis* oocysts and then sensitized by subcutaneous injection of *Mycobacterium bovis* sensitinogen (USDA). Donors for PPD were given only *M. bovis* sensitinogen. Keyhole limpet hemocyanin (KLH) $TF_d$ donors were given 8 mg of KLH in Freund's complete adjuvant. About 30 days after sensitization the donor animals were tested for Cell-mediated immunity (CMI) reactivity against the test antigens. Skin reactions greater than 9.0 mm in diameter at 48 hr and lymphocyte stimulation indexes (SI) greater than 1.50 ($>50\%$ above controls) were considered positive for donor selection.

$TF_d$ Preparation

Donor cattle were killed, then the mesenteric, thoracic, submandibular, cervical, auxillary, prefemoral and popliteal lymph nodes were removed from donor cattle. Crude $TF_d$ was isolated from the tissue according to the procedure previously described. Briefly, $TF_d$ was prepared by incubation of the lymphocytes in Hank's balanced salt solution for a period of 4 hr. at 37° C. Cell viability by trypan blue exclusion decreased by 60 to 70% during this incubation period. Following centrifugation the supernatant culture fluid, free of cells and cellular debris, was dialyzed against deionized water for 16 to 18 hr at 4° C. The dialysate was lyophilized, and the resulting dry material was designated "unfractionated $TF_d$". Approximately $10^6$ lymphocytes yielded 2.0 mg (Dry wt. of $TF_d$). The dose of $TF_d$ for a 74-kg recipient animal was 400 mg (the amount extracted from $2.0 \times 10^8$ lymphocytes). The $TF_d$ was dissolved in 5 ml of deionized water (ph 6.0 to 6.5) and given by intraperitoneal injection.

Alcohol-fractionated $TF_d$ $TF_d$ was fractionated with 95% ethanol by first dissolving the $TF_d$ at a concentration of 50 mg/ml in deionized water and then chilling the $TF_d$ solution at 4° C. All steps in the fractionation procedure were done at 4° C. from this point. Two volumes of alcohol were added dropwise to the $TF_d$ solution so that an alcohol-water interface was developed. After gentle mixing by stirring, the first precipitate developed immediately. It was fine and fibrous, or strand-like, in appearance. At the end of 1 hour, the precipitate was removed by centrifugation (700 g for 15 min). The supernatant was carefully separated from the precipitate by decantation. The pelleted precipitate was thoroughly drained to remove residual alcohol and then dissolved in deionized water and lyophilized.

Two volumes of ethanol were added to the supernatant, and the solution was mixed by gentle stirring. Precipitate was visible within an hour after the addition of the alcohol but appeared to require a longer precipitation time. After overnight (14–16 hr) extraction, the precipitate was collected by centrifugation and separated from the supernatant. The drained precipitate (designated "second precipitate") was dissolved in deionized water and lyophilized. In contrast to the first precipitate, the second was not fine and fibrous but more flaky and amorphous in appearance. Also, after centrifugation the second precipitate had a greater tendency than the first to stick to the glass wall of the centrifuge tube.

The supernatant from the second precipitate was lyophilized after removing the second precipitate. In Transfer experiments, the three fractions of the $TF_d$ were tested at concentrations equivalent to 400 mg of unfractionated $TF_d$. The three fractions were tested for CMI transfer as combined precipitates, second precipitate only, and supernatant.

Antigen and skin tests

*E. bovis* antigens were prepared as previously described from oocysts. PPD was prepared from *Mycobacterium bovis* at the Veterinary Service Laboratories, Animal and Plant Health Inspection Service, USDA, Ames, Iowa. KLH antigen was obtained from Dr. Dennis Burger, Veteran's Administration Hospital, Portland, Oregan. Cattle were skin tested by intradermal injection of 0.1 ml. in the cervical region and skin reactions were read at 24 and 48 hr. The skin test doses used were 800 μg for *E. bovis* antigen, 16 μg for PPD, and 350 μg for PPD, and 350 μg for KLH. The area of the test site was rotated when animals were tested more than once.

Lymphocyte stimulation assay

The semimicro protein synthesis assay for early detection of blastogenesis was used as previously described. Lymphocytes were obtained from peripheral blood using Ficoll-sodium metrizoate. Lymphocyte cultures were plated at a concentration of $2.0 \times 10^5$ cells/well and incubated at 37° C. for 36 hr. in 5% $CO_2$. After the incubation, 1 μCi of $^3$H-leucine was added to each culture. After 4 hr the cultures were harvested with a semiautomatic multiple sample processor. The incorporation of $^3$H-leucine was measured in a scintillation spectrophotometer and was expressed as counts per minute (CPM) for quadruplicate cultures. The stimulation index (SI) reported was obtained by dividing the average CPM with antigen by the average CPM of control cultures without antigen. For each antigen test, at least 4 concentrations ranging from 6.0 to 0.1 mg/culture were used in the blastogenesis assays to measure the optimal SI. Student's t test was used for determining the statistical differences between test and control cultures.

CMI transfer and assay schedule for $TF_d$

Within 5 days after CMI assay (pretest), $TF_d$ recipients were treated. The pretest CMI assay was measured to determine the existence of immunity to test antigens before $TF_d$ treatment. Stimulation of CMI against test antigens was determined 7 days after TFd treatment by CMI assay. The effect of $TF_d$ treatment was determined from the results of this assay (test).

The material produced by the process of this invention was tested in the manner indicated on Tables I, II, and III, which tables having originated in the "Bovine Transfer Factor: In Vivo Transfer of Cell-Mediated Immunity to Cattle with Alcohol Precipitates" by Phillip H. Klesius and H. Hugh Fudenberg, being publication No. 101 from the Department of Basic and Clinical Immunology and Microbiology, Medical University of South Carolina. Table I presents the data applicable to "unfractionated" TF, and Table II presents the corresponding data applicable to the alcohol fractionated work of the present invention. The data herein was obtained from cattle which were previously skin tested. Table III, unlike the previous two deals with the transfer of Cell-Mediated Immunity with alcohol fractionated Transfer Factor.

TABLE 1.

TRANSFER OF CMI WITH UNFRACTIONATED $TF_d$ IN CATTLE PREVIOUSLY SKIN TESTED

| | | Before $TF_d{}^a$ | | | | After $TF_d{}^b$ | | | |
|---|---|---|---|---|---|---|---|---|---|
| | | Blastogenesis: stimulation index | | Skin reaction: diameter of induration (mm) | | Blastogenesis: stimulation index | | Skin reaction: diameter of induration (mm) | |
| Treatment | Animal No. | E. bovis | $PPD^d$ | E. bovis | PPD | E. bovis | PPD | E. bovis | PPD |
| | 1 | 1.09 | 1.14 | 0.0 | 0.0 | $1.87^e$ | $3.65^e$ | 9.0 | 11.2 |
| Transfer | 2 | 0.91 | 1.01 | 0.0 | 0.0 | $5.88^e$ | $4.99^e$ | 9.1 | 6.6 |
| Factor | | | | | | | | | |
| | 3 | 1.01 | 0.95 | 0.0 | 0.0 | $3.44^e$ | $1.69^e$ | 12.8 | 12.4 |
| | 4 | 0.98 | 0.96 | 0.0 | 0.0 | $1.40^e$ | $1.26^g$ | 13.0 | 0.0 |
| | 5 | 1.00 | 0.96 | 0.0 | 0.0 | $1.06^f$ | $1.60^e$ | 12.3 | 13.0 |
| | 6 | 0.97 | 0.89 | 0.0 | 0.0 | 1.03 | 1.05 | 0.0 | 0.0 |
| | 7 | 1.00 | 1.05 | 0.0 | 0.0 | 1.08 | 1.04 | 0.0 | 0.0 |
| None | 8 | 1.04 | 1.09 | 0.0 | 0.0 | 0.99 | 0.94 | 0.0 | 0.0 |
| | 9 | 1.01 | 1.04 | 0.0 | 0.0 | 1.00 | 0.84 | 0.0 | 0.0 |

[a]Test reactions 5 days before TF treatment
[b]Test reactions 7 days after intraperitoneal injection of 400 mg of TF
[c]E. bovis antigen: Optimal antigen concentration for blastogenesis and 800 μg antigen for skin test.
[d]Purified protein derivative: Optimal antigen concentration for glastogenesis and 800 μg antigen for skin test.
[e]$p < 0.01$
[f]Not significant

TABLE II

TRANSFER OF CMI WITH ALCOHOL FRACTIONATED $TF_d$ IN CATTLE PREVIOUSLY SKIN TESTED

| | | Before $TF_d{}^a$ | | | | After $TF_d{}^b$ | | | |
|---|---|---|---|---|---|---|---|---|---|
| | | Blastogenesis: stimulation index | | Skin reaction: diameter of induration (mm) | | Blastogenesis: stimulation index | | Skin reaction: diameter of induration (mm) | |
| Treatment | Animal No. | E. bovis | $PPD^d$ | E. bovis | PPD | E. bovis | PPD | E. bovis | PPD |
| | 11 | 1.00 | 1.08 | 0.0 | 0.0 | $1.44^e$ | $1.34^f$ | 10.0 | 8.0 |
| Alcohol | 12 | 1.04 | 1.00 | 0.0 | 0.0 | $1.40^e$ | $6.57^e$ | 9.2 | 7.0 |
| Precipitates | | | | | | | | | |
| Combined | 13 | 1.00 | 1.00 | 0.0 | 0.0 | $1.72^e$ | $2.93^e$ | 8.2 | 0.0 |
| | 14 | 1.00 | 1.00 | 0.0 | 0.0 | $3.39^e$ | $3.20^e$ | 7.5 | 9.0 |
| | 15 | 0.98 | 0.92 | 0.0 | 0.0 | $1.31^f$ | $1.24^f$ | 9.0 | 9.0 |
| | 16 | 1.08 | 1.04 | 0.0 | 0.0 | $1.74^e$ | $2.05^e$ | 10.0 | 10.5 |
| | 17 | 1.11 | 1.01 | 0.0 | 0.0 | 0.89 | 0.96 | 0.0 | 0.0 |
| Alcohol | 18 | 0.89 | 1.00 | 0.0 | 0.0 | 0.91 | 1.05 | 0.0 | 0.0 |
| Supernatant | | | | | | | | | |
| | 19 | 1.08 | 1.07 | 0.0 | 0.0 | 1.05 | 0.96 | 0.0 | 0.0 |
| | 20 | 1.02 | 1.00 | 0.0 | 0.0 | 1.00 | 0.94 | 0.0 | 0.0 |

[a]Test reactions 5 days before treatment with TF-precipitate
[b]Test reactions 7 days after intraperitoneal injectin of TF-porecipitate, equivalent to 400 mg unfractionated TF
[c]E. bovis antigen: Optimal antigen concentration for blastogenesis and 800 μg antigen for skin test
[d]Purified protein derivative: Optimal antigen concentration for blastogenesis and 800 μg antigen for skin test.
[e]$p<0.01$
[f]$0.01 < p < 0.1$

TABLE

TRANSFER OF CMI WITH ALCOHOL FRACTIONATED $TF_d$

| | | Before $TF_d{}^a$ | | After $TF_d{}^b$ | | | | | |
|---|---|---|---|---|---|---|---|---|---|
| | | Blastogenesis: stimulation index | | Blastogenesis: stimulation index | | Skin reaction 7 days after treatment: diameter of induration (mm) | | Skin reaction 10 days after treatment: diameter of induration (mm) | |
| Treatment | Animal | E. bovis | $PPD^c$ | E. bovis | PPD | E. bovis | PPD | E. bovis | PPD |
| Alcohol Precipitates Combined | 21 | 1.03 | 1.09 | $1.62^d$ | $1.19^f$ | 0.0 | 0.0 | 10.0 | 8.0 |
| | 22 | 0.96 | 1.09 | $1.44^d$ | $1.16^f$ | 0.0 | 0.0 | 12.0 | 10.0 |
| | 23 | 1.00 | 1.00 | $1.27^e$ | $1.84^d$ | 0.0 | 0.0 | 9.0 | 8.9 |
| | 24 | 0.94 | 0.98 | $1.74^d$ | $1.40^d$ | 0.0 | 0.0 | 10.5 | 9.1 |
| Second Alcohol Precipitate | 25 | 1.04 | 1.01 | $2.80^d$ | $3.20^d$ | 12.0 | 12.4 | $ND^g$ | ND |
| | 26 | 1.10 | 0.93 | $2.08^d$ | $2.25^d$ | 18.5 | 15.0 | ND | ND |

$^a$Test reactions 5 days before treatment with TF precipitate, equivalent to 400 mg unfractionated TF
$^b$Test reactions 7 to 10 days after treatment
$^c$Purified protein derivative and E. bovis antigen: Optimal antigen concentration for blastogenesis and 800 μg antigen for skin test.
$^d$p <0.01
$^e$0.01 <p <0.1
$^f$Not significant
$^g$ND; not done

We claim:

1. An improved process for the preparation of a more efficient Bovine Transfer Factor which is useful in immunizing mammals by the transfer of cell-mediated immunity to *Eimeria bovis* antigen, purified protein derivative, and keyhole limpet hemocyanin and other antigens from pathogenic microbes or malignant tissues, the process comprising . . .
   (a) grinding a quantity of mesenteric, thoracic, submandibular, cervical, auxillary, prefemoral and popiteal lymphatic nodes from donor cattle,
   (b) incubating the material in Hank's salt solution for about 4 hours at 37° C.,
   (c) centrifuging the material to separate the desired liquid portion from the solids, which are discarded,
   (d) dialyzing the liquid to water for about from 16 to 18 hours at 4° C., to get rid of the unwanted materials, and retain an "unfractionated" Transfer Factor,
   (e) lyophilizing the TF to get rid of water,
   (f) adding dropwise a quantity of 95% alcohol at 4° C. until a fibrous interphase layer begins to develop,
   (g) allowing the interphase development to proceed undisturbed for about 1 hour, then stirring and centrifuging the mixture to separate precipitate Fraction I, which is insoluble in alcohol but soluble in water, from the liquid which is soluble in alcohol,
   (h) lyophilizing the precipitate to obtain final Fraction I,
   (i) repeating step (f) with the liquid of step (g),
   (j) repeating (g) and (h) to obtain precipitate Fraction II, which is soluble in water, and a liquid which is set aside, and
   (k) dissolving the precipitate in water and lyophilizing to obtain final precipitate Fraction II.

2. The process of claim 1 wherein alcohol of steps (f), (g), (i) and (j) is ethanol.

3. The process of claim 1 wherein the salts of Hank's solution is without sodium bicarbonate.

4. The process of claim 1 wherein the centrifuging of steps (c) and (g) are carried out at 700 g for about 15 minutes.

* * * * *